United States Patent
Bathija et al.

(10) Patent No.: US 12,085,554 B2
(45) Date of Patent: Sep. 10, 2024

(54) LOST CIRCULATION MATERIAL EVALUATION

(71) Applicant: Saudi Arabian Oil Company, Dhahran (SA)

(72) Inventors: Arpita Pal Bathija, Houston, TX (US); Ashok Santra, The Woodlands, TX (US)

(73) Assignee: Saudi Arabian Oil Company, Dhahran (SA)

( * ) Notice: Subject to any disclaimer, the term of this patent is extended or adjusted under 35 U.S.C. 154(b) by 300 days.

(21) Appl. No.: 17/664,169

(22) Filed: May 19, 2022

(65) Prior Publication Data
US 2023/0375523 A1 Nov. 23, 2023

(51) Int. Cl.
*G01N 33/28* (2006.01)
*E21B 21/00* (2006.01)

(52) U.S. Cl.
CPC ........ *G01N 33/2823* (2013.01); *E21B 21/003* (2013.01)

(58) Field of Classification Search
CPC .............. G01N 33/2823; G01N 33/00; G01N 33/2829; G01N 33/30; G01N 33/2888; E21B 21/003; E21B 21/00; E21B 21/01; E21B 21/06
See application file for complete search history.

(56) References Cited

U.S. PATENT DOCUMENTS

| | | |
|---|---|---|
| 1,811,799 A | 6/1931 | Lukens |
| 5,645,637 A | 7/1997 | Yaniv |
| 6,664,215 B1 | 12/2003 | Tomlinson |
| 7,497,258 B2 | 3/2009 | Savery et al. |
| 7,527,098 B2 | 5/2009 | Santra et al. |
| 7,637,319 B2 | 12/2009 | Savery et al. |

(Continued)

FOREIGN PATENT DOCUMENTS

| | | |
|---|---|---|
| WO | WO 2016053319 | 4/2016 |
| WO | WO 2019147559 | 8/2019 |

OTHER PUBLICATIONS

Alsaba et al., "Sealing Pressure Prediction Model for Lost Circulation Treatments Based on Experimental Investigations," AADE National Technical Conference and Exhibition, Apr. 2017, 7 pages.

(Continued)

*Primary Examiner* — Suman K Nath
(74) *Attorney, Agent, or Firm* — Fish & Richardson P.C.

(57) ABSTRACT

A lost circulation material is placed in a cavity. The cavity is defined by an inner bore of a cylindrical wall, intermediate of a piston and a screen. A distance between the piston and the screen is defined as the height of the cavity, which is adjustable. The piston is slid longitudinally, such that the piston comes in contact with the lost circulation material. The lost circulation material is heated to a specified test temperature mimicking a downhole temperature. A compression test is performed on the lost circulation material. The compression test includes flowing a test fluid into the cavity and applying force on the piston to pressurize the test fluid to a specified test pressure mimicking a downhole pressure. The force on the piston is released. The pressure of the test fluid and the height of the cavity are measured throughout the compression test.

19 Claims, 10 Drawing Sheets

(56) References Cited

U.S. PATENT DOCUMENTS

| | | | |
|---|---|---|---|
| 7,654,326 B1 | 2/2010 | Santra et al. | |
| 7,833,344 B2 | 11/2010 | Santra et al. | |
| 7,893,011 B2 | 2/2011 | Lewis et al. | |
| 8,418,763 B1 | 4/2013 | Deen et al. | |
| 9,023,150 B2 | 5/2015 | Brenneis et al. | |
| 9,617,460 B2 | 4/2017 | Reddy | |
| 9,708,869 B2 | 7/2017 | Sarmah et al. | |
| 10,150,905 B1 | 12/2018 | Reddy | |
| 11,148,977 B2 | 10/2021 | Thaemlitz et al. | |
| 11,531,006 B2 * | 12/2022 | Jandhyala | G01N 29/024 |
| 2010/0006288 A1 | 1/2010 | Santra et al. | |
| 2013/0192358 A1 * | 8/2013 | Murphy | G01N 33/2823 |
| | | | 73/152.05 |
| 2014/0102188 A1 * | 4/2014 | Murphy | G01N 33/2823 |
| | | | 73/152.05 |
| 2015/0033719 A1 | 2/2015 | Lawrence et al. | |
| 2021/0101833 A1 | 4/2021 | Thaemlitz et al. | |

OTHER PUBLICATIONS

Gerner, "Lost circulation experimental study in oil based mud and analyzing experimental data," These for the degree of Masters of Science, University of Stavanger, Jun. 2012, 62 pages.

Kumar et al., "Wellbore Strengthening: The Less-Studied Properties of Lost-Circulation Materials," SPE Annual Technical Conference and Exhibition, Sep. 2010, 13 pages.

Loeppke et al., "Design and evaluation of lost circulation materials for severe environments," 63rd Annual Technical Conference and Exhibition of the Society of Petroleum Engineers, Oct. 1988, 68 pages.

* cited by examiner

LOST CIRCULATION MATERIAL EVALUATION

TECHNICAL FIELD

This disclosure relates to evaluation of lost circulation materials.

BACKGROUND

Lost circulation in wells occurs when drilling fluid (commonly referred to as mud) flows into a subterranean formation instead of returning to the surface. Lost circulation can pose a serious problem during drilling of a well. Lost circulation materials are additives that can be included with drilling fluid to mitigate, prevent, and/or remediate seepage, partial, or severe loss of drilling fluid into a subterranean formation while drilling. Lost circulation materials are purposefully included in drilling fluid to increase particle size in order to plug thief zones, pores, and cracks which the drilling fluid itself cannot seal. Because drilling fluid pumps can handle up to a certain size of particles, the size of the openings that can be sealed using lost circulation materials is limited.

SUMMARY

This disclosure describes technologies relating to evaluation of lost circulation materials. Certain aspects of the subject matter described can be implemented as a method. A lost circulation material is placed in a cavity of an apparatus. A volume of the cavity is adjustable. The cavity is defined by an inner bore of a cylindrical wall of the apparatus, intermediate of a piston of the apparatus and a screen of the apparatus. A distance between the piston and the screen is defined as the height of the cavity. The height of the cavity is adjustable based on the piston sliding longitudinally within the inner bore away from or toward the screen. After placing the lost circulation material in the cavity, the piston is slid longitudinally, such that the piston comes in contact with the lost circulation material residing within the cavity. An initial height of the cavity is measured. The lost circulation material residing within the cavity is heated to a specified test temperature mimicking a downhole temperature. After the lost circulation material residing within the cavity has reached the specified test temperature, a compression test is performed on the lost circulation material residing within the cavity. The compression test includes flowing a test fluid into the cavity, such that the test fluid mixes with the lost circulation material residing within the cavity. The compression test includes applying force on the piston to pressurize the test fluid residing within the cavity to a specified test pressure mimicking a downhole pressure. The compression test includes releasing the force on the piston after the test fluid residing within the cavity has been pressurized to the specified test pressure. The compression test includes measuring pressure of the test fluid residing within the cavity. The pressure of the test fluid residing within the cavity is measured throughout the compression test. The compression test includes measuring the height of the cavity. The height of the cavity is measured throughout the compression test.

This, and other aspects, can include one or more of the following features. The method can include generating a plot of the measured pressures of the test fluid residing within the cavity as stress versus the measured heights of the cavity as strain for the compression test. The apparatus can include a first port. The first port can extend through the cylindrical wall. The test fluid can be flowed into the cavity through the first port by a pump. The force can be applied on a first end of the piston by a linear actuator. The pump flowing the test fluid and the linear actuator applying force on the piston can cooperate to pressurize the test fluid residing within the cavity to the specified test pressure mimicking the downhole pressure. The first port can be closed after flowing the test fluid into the cavity and prior to applying force on the piston, thereby preventing the test fluid from flowing out of the cavity through the first port. The apparatus can include a base. The base can be coupled to the cylindrical wall. At least a portion of the base can be disposed within the inner bore. The screen can be coupled to the base. The screen can span a cross-sectional area of the inner bore. The apparatus can include a second port. The second port can extend through the base. The second port can pass through the screen. The pressure of the test fluid residing within the cavity can be measured by a pressure sensor that is coupled to the second port. The apparatus can include a first sealing element. The first sealing element can wrap around the piston. The first sealing element can form a first seal between the piston and the cylindrical wall to prevent leakage of the test fluid from the cavity through the first seal. The first seal can remain intact while the piston slides longitudinally within the inner bore. The apparatus can include a second sealing element. The second sealing element can wrap around the portion of the base that is disposed within the inner bore. The second sealing element can form a second seal between the base and the cylindrical wall to prevent leakage of the test fluid from the cavity through the second seal. The method can include, after performing the compression test on the lost circulation material residing within the cavity, opening the first port and applying force on the piston to push the test fluid out of the cavity through the first port. The test fluid can be a drilling mud. The first port can be sized to prevent the lost circulation material from exiting the cavity through the first port. The lost circulation material can be heated to the specified test temperature mimicking the downhole temperature by a heater. The heater can be wrapped around an outer circumferential surface of the cylindrical wall. The method can include mitigating heat from the heater dissipating to a surrounding environment. The heat from the heater can be mitigated from dissipating to the surrounding environment by an insulating jacket. The insulating jacket can surround the heater.

Certain aspects of the subject matter described can be implemented as a system. The system includes an apparatus, a motor, a pump, a pressure sensor, a heater, and a computer. The apparatus includes a cylindrical wall, a screen, and a piston. The cylindrical wall defines an inner bore. The screen is disposed within the inner bore. The piston is sized to fit within the inner bore. A portion of the inner bore that is intermediate of the screen and the piston is defined as an inner volume of the apparatus for holding a lost circulation material and a test fluid. The inner volume is variable based on a longitudinal position of the piston within the inner bore relative to the screen. The motor is coupled to the piston. The pump is coupled to the cylindrical wall. The pressure sensor is coupled to the apparatus. The heater is coupled to the cylindrical wall. The computer includes a processor and a computer-readable storage medium. The processor is communicatively coupled to the motor, the pump, the heater, and the pressure sensor. The computer-readable storage medium is coupled to the processor. The computer-readable storage medium stores programming instructions for execution by the processor. The programming instructions instruct the processor to perform operations. The operations include transmitting a temperature adjustment signal to the heater to cause the heater to heat the lost circulation material residing within the inner volume to a specified test temperature mimicking a downhole temperature. The operations include performing a compression test on the lost circulation material residing within the inner volume. The compression test includes transmitting a pumping signal to the pump to cause the pump to flow the test fluid into the inner volume, such that the test fluid mixes with the lost circulation material residing within the inner volume. The compression test includes transmitting a start signal to the motor to cause the motor to apply force on the piston to slide the piston longitudinally within the inner bore toward the screen, thereby pressurizing the test fluid and the lost circulation material residing within the inner volume to a specified test pressure mimicking a downhole pressure. The compression test includes, after the test fluid and the lost circulation material residing within the inner volume have been pressurized to the specified test pressure, transmitting a stop signal to the motor to cause the motor to release the force on the piston, thereby allowing the test fluid and the lost circulation material residing within the inner volume to de-pressurize. The compression test includes, throughout the compression test, receiving a position signal from the motor. The position signal represents a longitudinal position of the piston within the inner bore relative to the screen. The compression test includes, throughout the compression test, determining and recording, to the computer-readable storage medium, a height of the inner volume based on the received position signal from the motor. The compression test includes, throughout the compression test, receiving a pressure signal from the pressure sensor. The pressure signal represents an operating pressure of the test fluid and the lost circulation material residing within the inner volume. The compression test includes, throughout the compression test, recording the operating pressure of the test fluid and the lost circulation material residing within the inner volume to the computer-readable storage medium.

This, and other aspects, can include one or more of the following features. The operations can include generating a plot of the recorded pressures as stress versus the recorded heights of the inner volume as strain for the compression test. The operations can include displaying the plot on a screen that is communicatively coupled to the processor. The apparatus can include a base. The base can be coupled to the cylindrical wall. At least a portion of the base can be disposed within the inner bore. The apparatus can include a first O-ring. The first O-ring can wrap around an outer circumferential wall of the piston. The apparatus can include a second O-ring. The second O-ring can wrap around the portion of the base that is disposed within the inner bore. The heater can wrap around an outer circumferential surface of the cylindrical wall. The system can include an insulating jacket. The insulating jacket can surround the heater. The insulating jacket can be configured to mitigate heat from the heater dissipating to a surrounding environment. The base can be coupled to the cylindrical wall by a threaded bolt. The system can include a reservoir that is configured to hold a specified amount of the test fluid. The system can include a piping network. The piping network can include a suction piping that fluidically connects the reservoir to the pump. The piping network can include a discharge piping that fluidically connects the pump to the cylindrical wall. The piping network can include a bypass piping. The bypass piping can fluidically connect the reservoir to the cylindrical wall. The bypass piping can be configured to flow test fluid from the inner volume back to the reservoir. The test fluid can be a drilling mud.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

Figure 1A:
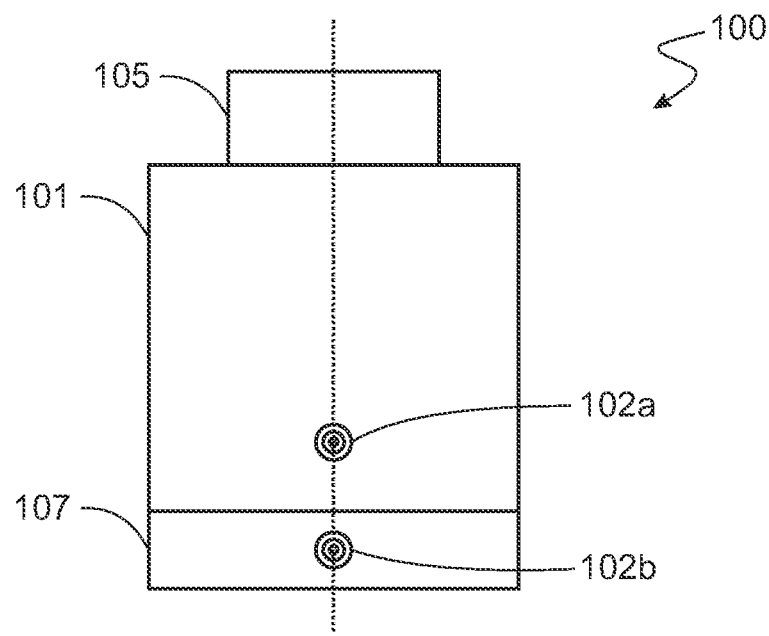
FIG. 1A is a front view of an example apparatus that can be used to evaluate a lost circulation material with its piston in a retracted position.

Drilling fluid is used to aid the drilling of boreholes in the Earth. Some functions of drilling fluids include providing hydrostatic pressure to prevent formation fluids from entering the wellbore, keeping the drill bit cool and clean during drilling operations, and carrying/suspending drill cuttings. Lost circulation is the loss of drilling fluids into the subterranean formation in which the well is being drilled. Lost circulation is a major challenge in the oil and gas industry, as it can cause significant costs due to fluid loss, non-productive downtime, bypassed reserves, sidetrack wells, and abandoned wells. Wellbore strengthening materials, such as lost circulation materials (LCMs), can be used to mitigate and/or prevent lost circulation. Depending on the size of fractures, the LCM is selected and mixed with drilling fluids to treat the targeted zone. Knowledge of the properties of the LCM selected in similar or the same conditions as the zone in which they are to be flowed can result in greater success in strengthening the wellbore and preventing lost circulation. For example, mechanical properties like resiliency can dictate the packing efficiency of an LCM, especially during pressurization and de-pressurization cycles while drilling a wellbore.

This disclosure describes evaluation of wellbore strengthening materials, such as lost circulation materials. An apparatus is used to evaluate a lost circulation material in the presence of drilling fluid at high pressure and high temperature to mimic downhole conditions. The apparatus includes a motor and a piston to provide and measure a continuous (as opposed to step-wise or discrete) stress-strain relationship of the lost circulation material as pressure is applied. The apparatus also includes a heater and insulation, so that experiments may be performed at elevated temperature to mimic downhole conditions. The apparatus can be used to measure resiliency of the lost circulation material, which is an extent to which the lost circulation material rebounds once an applied load is removed.

The subject matter described in this disclosure can be implemented in particular implementations, so as to realize one or more of the following advantages. By implementing the apparatuses, systems, and methods described herein, LCM properties (such as resiliency) can be evaluated in the presence of drilling fluids and exposure to operation conditions (such as temperature and pressure) that mimic downhole conditions, which can be beneficial in learning how the LCM will actually behave downhole while drilling. The downhole conditions can be mimicked, for example, in a laboratory setting. By implementing the apparatuses, systems, and methods described herein, data can be continuously obtained (for example, continuous pressure (stress) data and continuous compaction/expansion (strain) data) as opposed to collection of discrete data, which can be inaccurate and imprecise due to its inability to capture fast/sudden changes in the evaluated material.

Figure 1B:
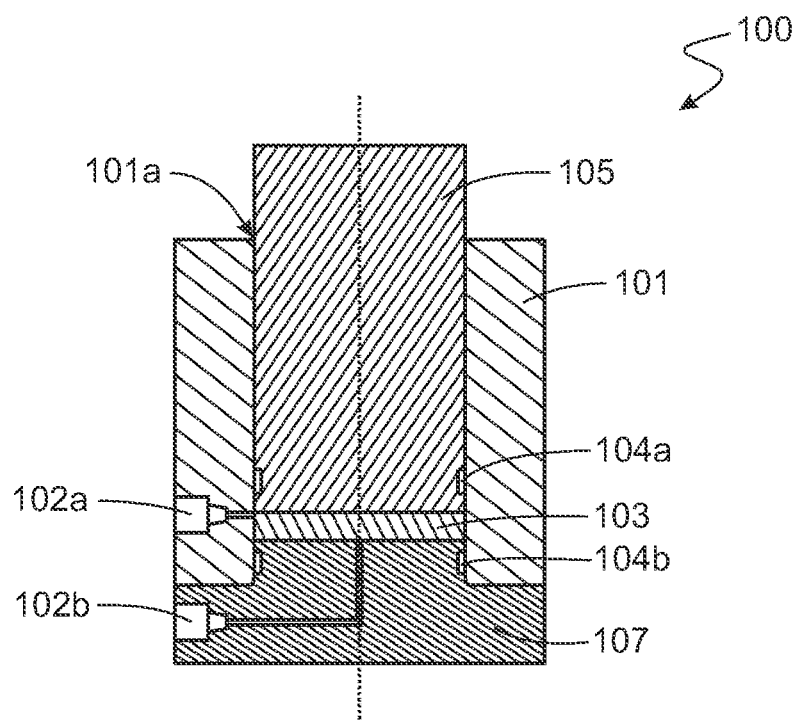
FIG. 1B is a cross-sectional view of the apparatus of FIG. 1A.
Figure 1C:
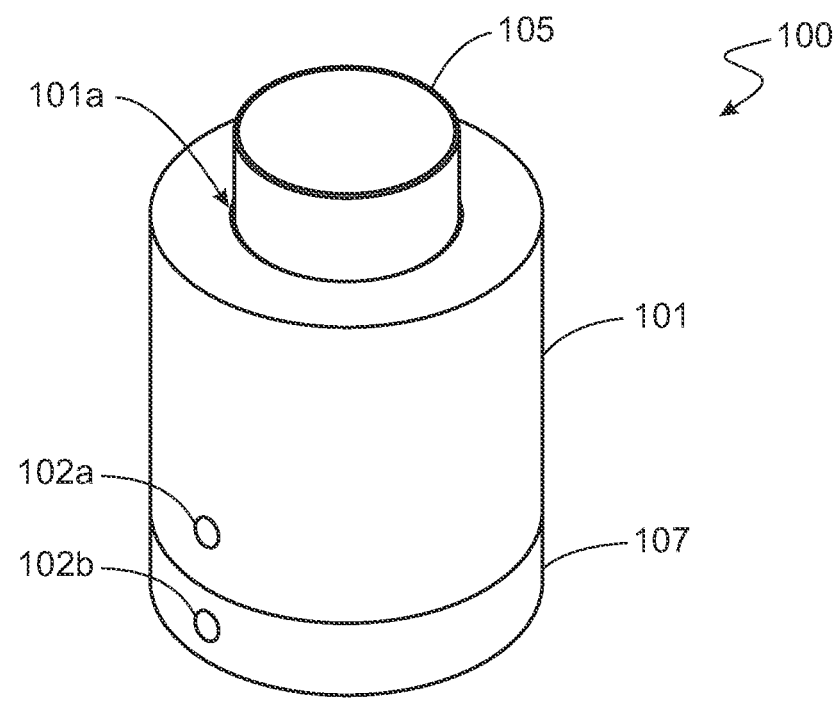
FIG. 1C is a perspective view of the apparatus of FIG. 1A.
Figure 1D:
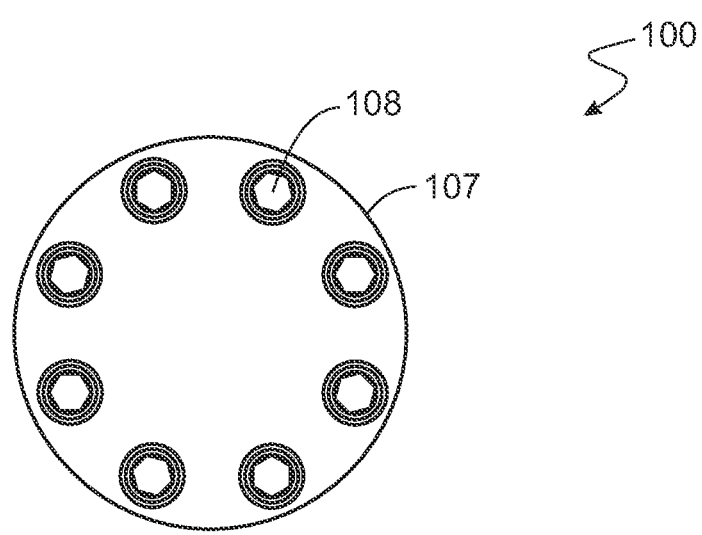
FIG. 1D is a bottom view of the apparatus of FIG. 1A.
Figure 1E:
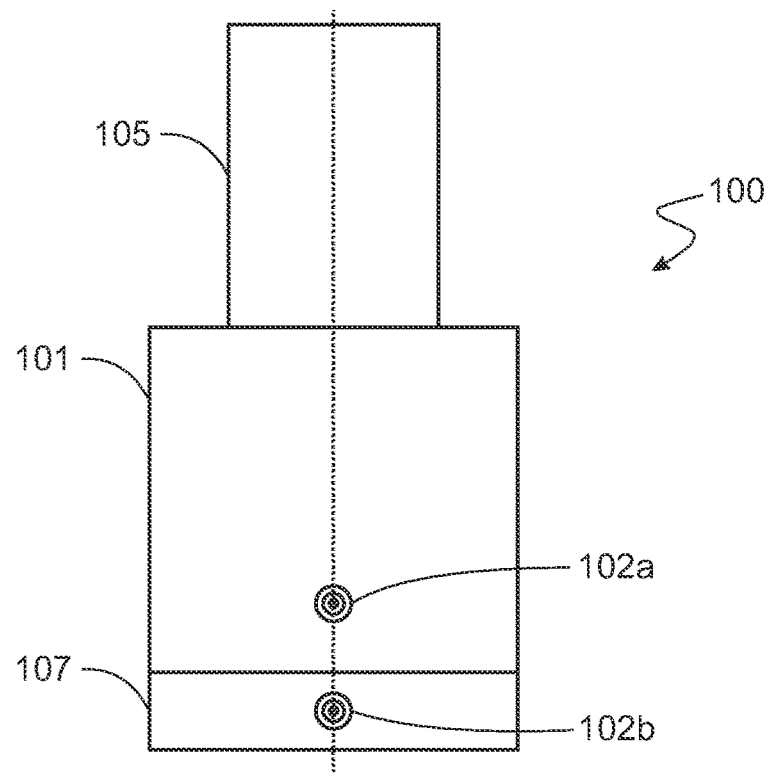
FIG. 1E is a front view of the apparatus of FIG. 1A with its piston in an extended position.
Figure 1F:
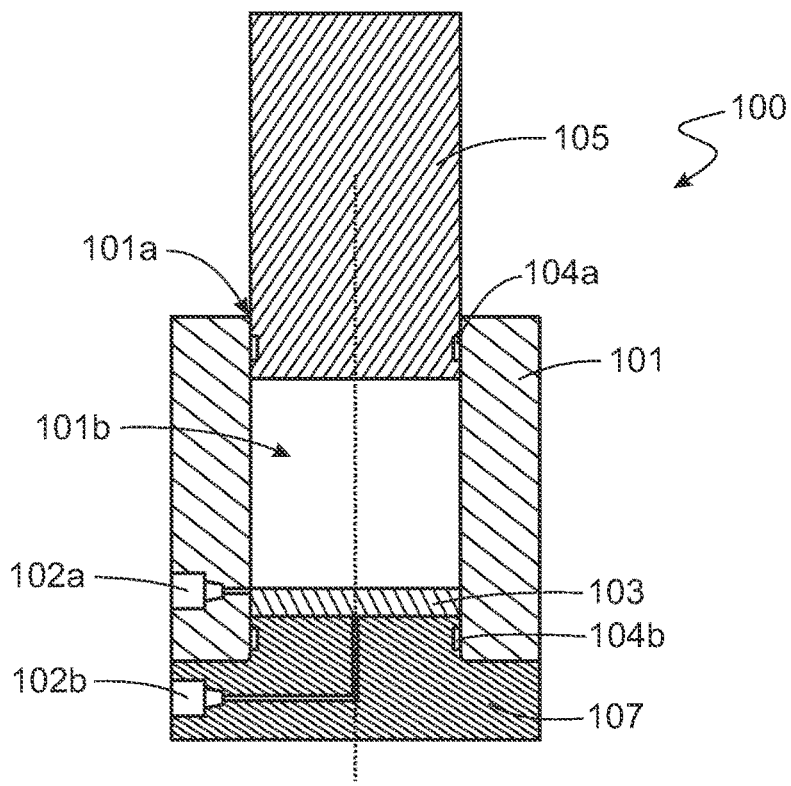
FIG. 1F is a cross-sectional view of the apparatus of FIG. 1E.

FIG. 1A is a front view of an apparatus 100 that can be used to evaluate a lost circulation material. FIGS. 1B, 1C, and 1D are a cross-sectional view, a perspective view, and a bottom view of the apparatus 100, respectively. The apparatus 100 includes a cylindrical wall 101, a screen 103, and a piston 105. The cylindrical wall 101 defines an inner bore 101a. The screen 103 is disposed within the inner bore 101a. The piston 105 is sized to fit within the inner bore 101a. An outer, circumferential surface of the piston 105 can complement an inner, circumferential surface of the cylindrical wall 101. For example, a diameter of the piston 105 is slightly smaller than a diameter of the inner bore 101a, such that the piston 105 can slide longitudinally within the inner bore 101a along a longitudinal axis (dotted line) of the cylindrical wall 101. A portion of the inner bore 101a that is intermediate of the screen 103 and the piston 105 is defined as an inner volume 101b of the apparatus 100. The inner volume 101b can hold a lost circulation material 110 and a test fluid 111. The inner volume 101b is variable based on a longitudinal position of the piston 105 within the inner bore 101a relative to the screen 103. For example, the piston 105 can slide longitudinally within the inner bore 101a to adjust the size of the inner volume 101b. The screen 103 can span (that is, cover) a cross-sectional area of the inner bore 101a. The screen 103 can be configured to prevent leakage of fluid from the inner volume 101b through the screen 103. FIGS. 1A, 1B, and 1C depict the apparatus 100 with its piston 105 in a retracted position in which the piston 105 is in direct physical contact with the screen 103. FIGS. 1E and 1F are a front view and a cross-sectional view, respectively, of the apparatus 100 with its piston 105 in an extended position in which the piston 105 is not in direct physical contact with the screen 103.

The lost circulation material 110 is a material that is designed to be used in a downhole environment (for example, a subterranean zone of a well) to prevent the loss of drilling fluid into a subterranean formation. The lost circulation material 110 can be included with a drilling fluid that is used to drill a well. The lost circulation material 110 can be, for example, fibrous (cedar bark, shredded cane stalks, mineral fiber, or hair), flaky (mica flakes, pieces of plastic, or cellophane sheeting), or granular (ground and sized limestone or marble, wood, nut hulls, Formica, corncobs, or cotton hulls). The test fluid 111 can be a fluid that is typically encountered in downhole environments. For example, the test fluid 111 can be the drilling fluid with which the lost circulation material 110 is to be flowed to drill the well. For example, the test fluid 111 is a drilling mud, such as a water-based drilling mud, oil-based drilling mud, or synthetic-based drilling mud.

The cylindrical wall 101 and the piston 105 are made of materials that are resistant to corrosion when exposed to fluids that are typically encountered in downhole environments (for example, subterranean zones of wells). The cylindrical wall 101 and the piston 105 are made of materials that are resistant to damage (for example, deformation) when exposed to pressures that are typically encountered in downhole environments (for example, pressures greater than 2,000 pounds per square inch gauge (psig), 4,000 psig, 6,000 psig, 10,000 psig, 12,000 psig, or 14,000 psig). The cylindrical wall 101 and the piston 105 are made of materials that are resistant to damage when exposed to temperatures that are typically encountered in downhole environments (for example, temperatures greater than 100 degrees Fahrenheit (° F.), 200° F., 300° F., or 400° F.). The cylindrical wall 101 can be made of a metal or an alloy including a metal. For example, the cylindrical wall 101 can be made of any grade of alloy steel (such as stainless steel or carbon steel), a nickel alloy (such as Hastelloy), or chromium alloy (such as chrome moly). The piston 105 can be made of a metal or an alloy including metal. For example, the piston 105 can be made of an iron alloy or a nickel alloy. In some implementations, the cylindrical wall 101 and the piston 105 are made of the same material (for example, Hastelloy). The screen 103 is made of a material that is resistant to damage when exposed to pressures and temperatures that are typically encountered in downhole environments. The screen 103 is made of a material that can serve as a barrier for preventing leakage of fluids (for example, the test fluid 111) from the inner volume 101b. The screen 103 is configured to prevent leakage of material (such as the lost circulation material 110) from the inner volume 101b. Leakage of such material is undesired as it may potentially block a fluid path, for example, for the test fluid 111 to flow, which can prevent pore pressure adjustments within the inner volume 101b. In some implementations, the screen 103 can be made of a ceramic material (such as quartz, clay, or sand) or metal (such as stainless steel or carbon steel).

The apparatus 100 can include a base 107. In some implementations, the base 107 is coupled to the cylindrical wall 101. For example, the base 107 can be coupled to the cylindrical wall 101 by a threaded bolt 108. Although the example shown in FIG. 1D depicts the base 107 coupled to the cylindrical wall 101 by multiple threaded bolts 108, the base 107 can be coupled to the cylindrical wall 101 by alternative or additional mechanisms, such as by an adhesive. In some implementations, at least a portion of the base 107 is disposed within the inner bore 101a. For example, an outer, circumferential surface of the portion of the base 107 disposed within the inner bore 101a can complement an inner, circumferential surface of the cylindrical wall 101. For example, an outer diameter of the portion of the base 107 disposed within the inner bore 101a is slightly smaller than the diameter of the inner bore 101a, so that the portion of the base 107 disposed within the inner bore 101a can fit snugly within the inner bore 101a. In some implementations, the screen 103 is coupled to the base 107.

The apparatus 100 can include a first port 102a. The first port 102a can extend through the cylindrical wall 101. In some implementations, the first port 102a can switch from an open position and a closed position. For example, the first port 102a can be blinded by a blind flange in the closed position, and the blind flange can be removed to switch the first port 102a to the open position. For example, the first port 102a can include a valve that can be closed to switch the first port 102a to the closed position and opened to switch the first port 102a to the open position. The first port 102a can be configured to allow fluid (for example, the test fluid 111) to enter or exit the inner volume 101b through the first port 102a while the first port 102a is in the open position. For example, the test fluid 111 can be allowed to flow into the inner volume 101b through the first port 102a while the first port 102a is in the open position. For example, the first port 102a can be switched to the closed position during a test for evaluating the lost circulation material 110 to prevent the test fluid 111 from exiting the inner volume 101b. For example, the first port 102a can be switched to the open position after the test for evaluating the lost circulation material 110 has completed to allow the test fluid 111 to be evacuated from the inner volume 101b. The first port 102a can be positioned on the cylindrical wall 101 at a longitudinal position along the longitudinal axis (dotted line) that is intermediate of the screen 103 and the piston 105. In some implementations, the first port 102a is positioned on the cylindrical wall 101 at a longitudinal position along the longitudinal axis (dotted line) that is about 1 millimeter away from the screen 103. In some implementations, the first port 102a is positioned on the cylindrical wall 101 at a longitudinal position along the longitudinal axis (dotted line), such that an edge of the first port is tangent to the screen 103. In some implementations, the first port 102a is sized to prevent the lost circulation material 110 from exiting the inner volume 101b through the first port 102a, regardless of whether the first port 102a is in the open position or the closed position. For example, the first port 102a can have a bore size that is sufficiently small to prevent solid particulates having an average diameter equal to or greater than 8.9 mm from traveling through the first port 102a.

Figure 2A:
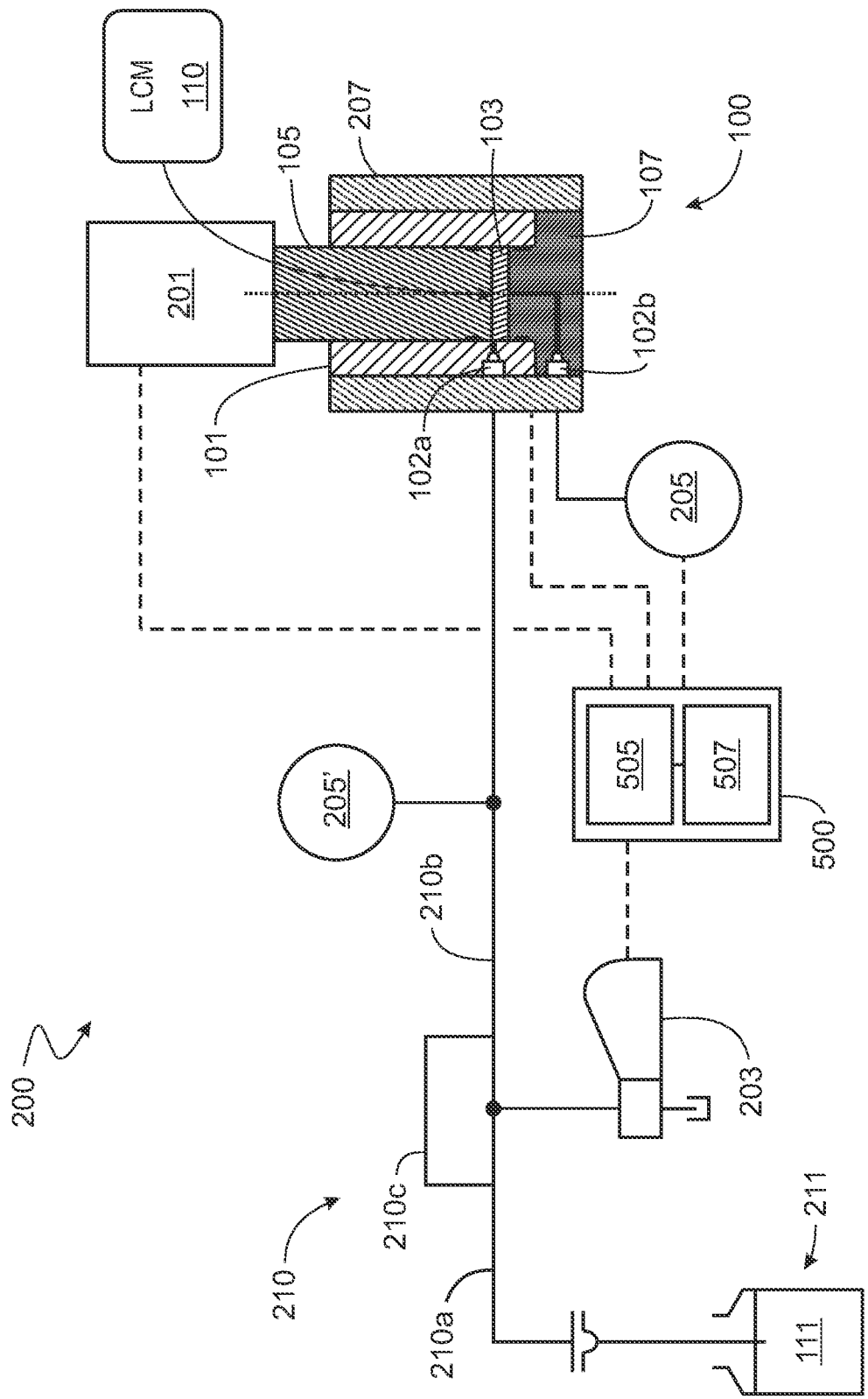
FIG. 2A is a schematic diagram of a system that includes the apparatus of FIG. 1A.

The apparatus 100 can include a second port 102b. The second port 102b can extend through the base 107. The second port 102b can pass through the screen 103. The second port 102b can be configured to allow fluid (for example, the test fluid 111) to enter or exit the inner volume 101b through the second port 102b. The second port 102b can couple to a pressure sensor (an example is shown in FIG. 2A). For example, the second port 102b can be coupled to a pressure sensor to establish fluid communication between the pressure sensor and the inner volume 101b, such that the pressure sensor can measure a fluidic pressure of the inner volume 101b (such as the operating pressure of the test fluid 111 residing within the inner volume 101b).

The apparatus 100 can include a first sealing element 104a. The first sealing element 104a can wrap around the outer, circumferential surface of the piston 105. The first sealing element 104a can form a first seal between the piston 105 and the cylindrical wall 101 to prevent leakage of fluid (for example, the test fluid 111) from the inner volume 101b through the first seal. For example, the first sealing element 104a seals against the outer, circumferential surface of the piston 105 and the inner, circumferential surface of the cylindrical wall 101 to form the first seal. In some implementations, the first sealing element 104a is a first O-ring that is coupled to the outer, circumferential surface of the piston 105. The first sealing element 104a can be fixed in position relative to the piston 105 and move with the piston 105 as the piston 105 slides longitudinally within the inner bore 101a. The first seal can be configured to remain intact (that is, the first seal does not break) while the piston 105 slides longitudinally within the inner bore 101a. The first sealing element 104a can be made of an elastomer, such as a fluoroelastomer. For example, the first sealing element 104a can be made of a fluoroelastomer including vinylidene fluoride (VDF) and hexafluoropropylene (HFP); a fluoroelastomer including VDF, HFP, and tetrafluoroethylene (TFE); a fluoroelastomer including VDF, TFE, and perfluoromethylvinylether (PMVE); a fluoroelastomer including propylene, TFE, and VDF; or a fluoroelastomer including VDF, HFP, TFE, PMVE, and ethylene.

The apparatus 100 can include a second sealing element 104b. The second sealing element 104b can wrap around the outer, circumferential surface of the portion of the base 107 disposed within the inner bore 101a. The second sealing element 104b can form a second seal between the portion of the base 107 disposed within the inner bore 101a and the cylindrical wall 101 to prevent leakage of fluid (for example, the test fluid 111) from the inner volume 101b through the second seal. For example, the second sealing element 104b seals against the outer, circumferential surface of the portion of the base 107 disposed within the inner bore 101a and the inner, circumferential surface of the cylindrical wall 101 to form the second seal. In some implementations, the second sealing element 104b is a second O-ring that is coupled to the outer, circumferential surface of the portion of the base 107 disposed within the inner bore 101a. The second sealing element 104b can be made of an elastomer, such as a fluoroelastomer. For example, the second sealing element 104b can be made of a fluoroelastomer including VDF and HFP; a fluoroelastomer including VDF, HFP, and TFE; a fluoroelastomer including VDF, TFE, and PMVE; a fluoroelastomer including propylene, TFE, and VDF; or a fluoroelastomer including VDF, HFP, TFE, PMVE, and ethylene.

FIG. 2A is a schematic diagram of a system 200 that includes the apparatus 100. The system 200 includes the apparatus 100, a motor 201, a pump 203, a pressure sensor 205, a heater 207, and a computer 500. The motor 201 is coupled to the piston 105. For example, the piston 105 includes a first end and a second end that is opposite the first end. The second end can be closer in proximity to the screen 103 in comparison to the first end, and the motor 201 can be coupled to the first end of the piston 105. The motor 201 is configured to adjust a longitudinal position of the piston 105 within the inner bore 101a, thereby adjusting a size of the inner volume 101b. The motor 201 can be, for example, a linear actuator that couples to the piston 105 and translates the piston 105 longitudinally within the inner bore 101b by applying force on the piston 105. The motor 201 can cause the piston 105 to slide longitudinally within the inner bore 101b toward the screen 103, thereby reducing the height of the inner volume 101b. The motor 201 can cause the piston 105 to slide longitudinally within the inner bore 101b away from the screen 103, thereby increasing the height of the inner volume 101b. The pump 203 is coupled to the cylindrical wall 101. For example, the pump 203 is coupled to the first port 102a. The pump 203 is configured to flow the test fluid 111 into the inner volume 101b, for example, through the first port 102a in the open position. The motor 201 and the pump 203 can be cooperatively configured to pressurize the test fluid 111 residing within the inner volume 101b to a specified test pressure that mimics a downhole pressure. The specified test pressure can be in a range of from about 1 psig to about 16,000 psig, from about 2,000 psig to about 16,000 psig, from about 4,000 psig to about 16,000 psig, from about 6,000 psig to about 16,000 psig, from about 8,000 psig to about 16,000 psig, from about 10,000 psig to about 16,000 psig, from about 12,000 psig to about 16,000 psig, or from about 14,000 psig to about 16,000 psig.

The pressure sensor 205 is coupled to the apparatus 100. For example, the pressure sensor 205 is coupled to the second port 102b. The pressure sensor 205 is configured to receive a portion of the test fluid 111 from the inner volume 101b through the second port 102b and measure a pressure of the test fluid 111 residing within the inner volume 101b. As shown in FIG. 2A, the system 200 can include additional pressure sensors. For example, the system 200 can include a pressure sensor 205' at the discharge of the pump 203 for monitoring the pressure of the test fluid 111 entering the inner volume 101b. The heater 207 is coupled to the cylindrical wall 101. For example, the heater 207 wraps around an outer, circumferential surface of the cylindrical wall 101. The heater 207 is configured to heat any material (for example, the lost circulation material 110, the test fluid 111, or both) residing within the inner volume 101b to a specified test temperature that mimics a downhole temperature. The specified test temperature can be in a range of from about 100° F. to about 400° F., from about 200° F. to about 400° F., or from about 300° F. to about 400° F. The heater 207 can be, for example, an electric heater that includes an electric resistor (such as nichrome, Kanthal, or cupronickel) that produces heat in response to receiving electrical power.

Figure 5:
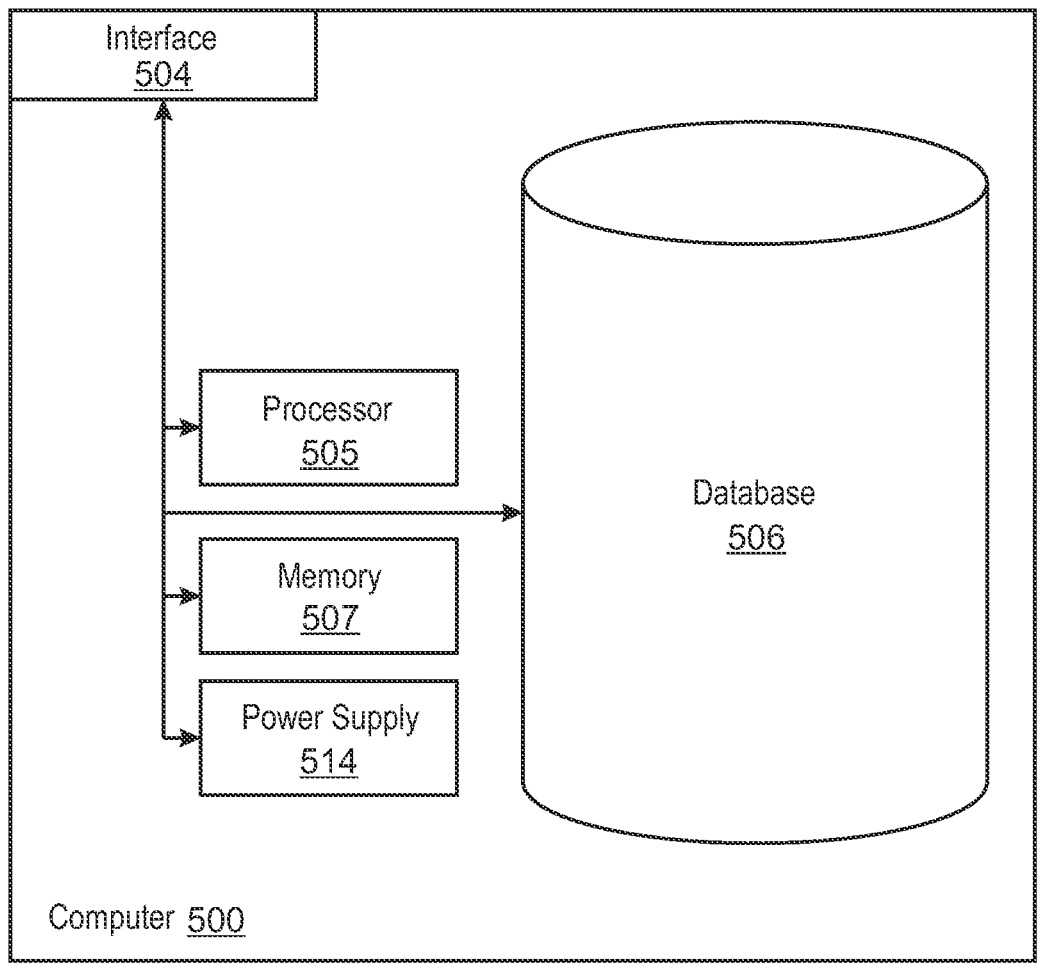
FIG. 5 is a block diagram of an example computer system.

The computer 500 includes a processor 505 and a memory 507. The processor 505 is communicatively coupled to the motor 201, the pump 203, the pressure sensor 205, and the heater 207. The memory 507 is a computer-readable storage medium that is coupled to the processor 505 and stores programming instructions for execution by the processor 505. The programming instructions instruct the processor 505 to perform operations. The operations can include transmitting a temperature adjustment signal to the heater 207 to cause the heater 207 to heat the lost circulation material 110 residing within the inner volume 101b to a specified test temperature that mimics a downhole temperature. The operations can include performing a compression test on the lost circulation material 110 residing within the inner volume 101b. The compression test can include transmitting a pumping signal to the pump 203 to cause the pump 203 to flow the test fluid 111 into the inner volume 101b, such that the test fluid 111 mixes with the lost circulation material 110 residing within the inner volume 101b. The compression test can include transmitting a start signal to the motor 201 to cause the motor 201 to apply force on the piston 105 to slide the piston 105 longitudinally within the inner bore 101b toward the screen 103, thereby pressurizing the lost circulation material 110 and the test fluid 111 residing within the inner volume 101b to a specified test pressure that mimics a downhole pressure. The compression test can include, after the lost circulation material 110 and the test fluid 111 residing within the inner volume 101b have been pressurized to the specified test pressure, transmitting a stop signal to the motor 201 to cause the motor 201 to release the force on the piston 105, thereby allowing the lost circulation material 110 and the test fluid 111 residing within the inner volume 101b to depressurize (relax/expand). The operations can include, throughout the compression test, receiving a position signal from the motor 201. The position signal can represent a longitudinal position of the piston 105 within the inner bore 101b relative to the screen 103. The operations can include, throughout the compression test, determining and recording (to the memory 507) a height of the inner volume 101b based on the received position signal from the motor 201. The operations can include, throughout the compression test, receiving a pressure signal from the pressure sensor 205. The pressure signal can represent an operating pressure of the lost circulation material 110 and the test fluid 111 residing within the inner volume 101b. The operations can include, throughout the compression test, recording (to the memory 507) the operating pressure of the lost circulation material 110 and the test fluid 111 residing within the inner volume 101b. The operations can include generating a plot of the recorded pressures (stress) versus the recorded heights of the inner volume (strain) for the compression test. The operations can include displaying the generated plot on a screen that is communicatively coupled to the processor 505. The computer 500 is also shown in FIG. 5 and is described in more detail later.

In some implementations, the system 200 includes a piping network 210 and a reservoir 211. The reservoir 211 is configured to hold a specified amount of the test fluid 111. In some implementations, the reservoir 211 is sized to hold a minimum volume of the test fluid 111 in a range of from about 10 milliliters (mL) to about 100 mL (for example, a minimum volume of about 30 mL). The piping network 210 can include a suction piping 210a and a discharge piping 210b. The suction piping 210a fluidically connects the reservoir 211 to the pump 203. The discharge piping 210b fluidically connects the pump 203 to the cylindrical wall 101 (for example, the first port 102a). The test fluid 111 can flow from the reservoir 211 to the pump 203 via the suction piping 210a. The test fluid 111 can flow from the pump 203 into the inner volume 101b via the discharge piping 210b. The piping network 210 can include a bypass piping 210c. The bypass piping 210c can fluidically connect the reservoir 211 to the cylindrical wall 101 (for example, the first port 102a). The bypass piping 210c bypasses the pump 203, such that fluid (for example, the test fluid 111) can flow from the inner volume 101b back to the reservoir 211. While the pump 203 flows the test fluid 111 from the reservoir 211 into the inner volume 101b, the bypass piping can be closed (for example, by a blind flange or a valve). While the test fluid 111 flows from the inner volume 101b back to the reservoir 211 via the bypass piping 210c, the suction piping 210a, the discharge piping 210b, or both can be closed (for example, by a blind flange or a valve).

Figure 2B:
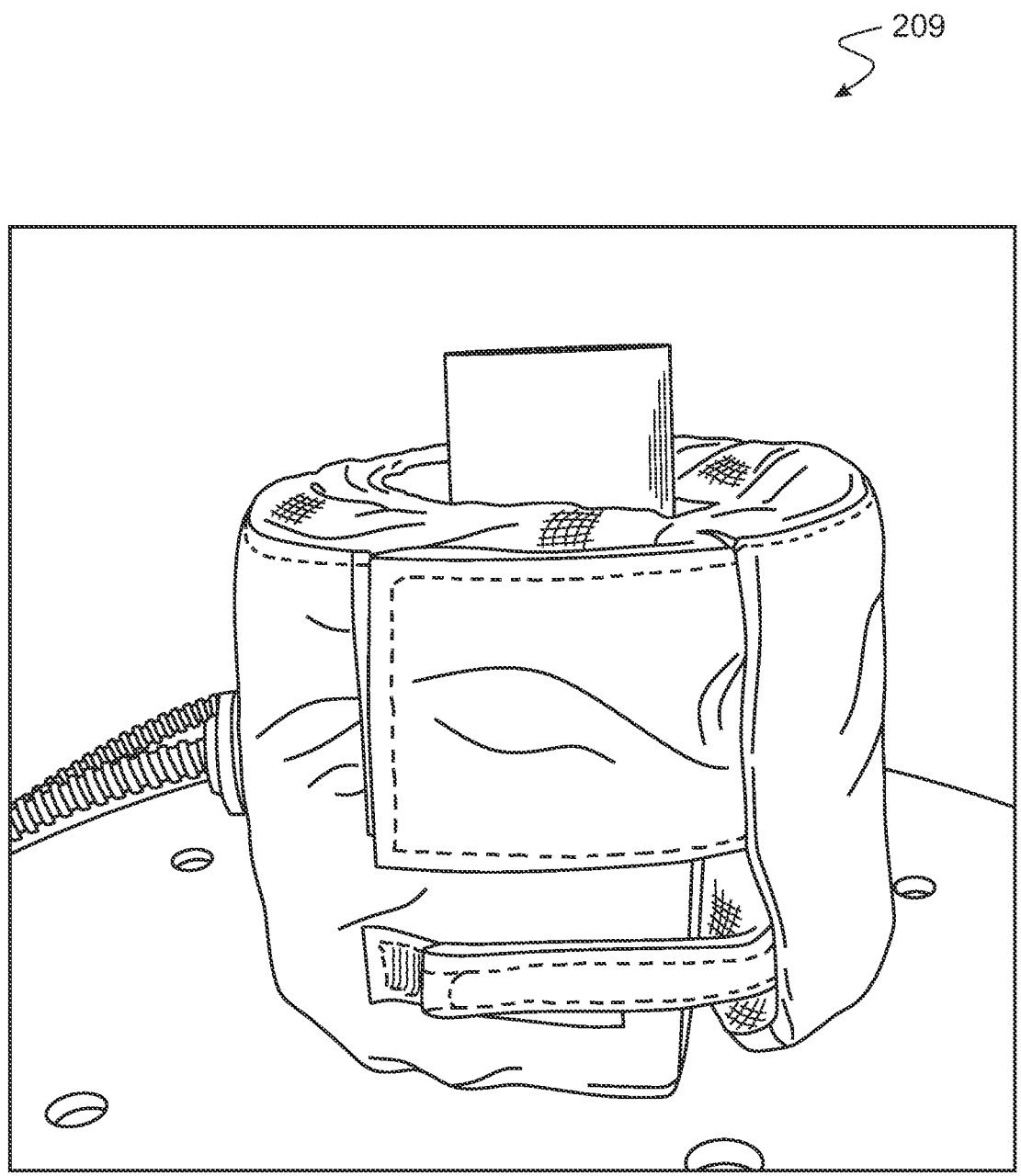
FIG. 2B is a photograph of an example insulation jacket that can surround the apparatus of FIG. 1A.

FIG. 2B is a photograph of an example insulation jacket 209 that can be included in the system 200 shown in FIG. 2A. The insulation jacket 209 can surround at least a portion of the apparatus 100. For example, the insulation jacket 209 can surround the heater 207. The insulation jacket 209 can be configured to mitigate heat from the heater 207 dissipating to a surrounding environment. Thus, the insulation jacket 209 mitigates heat loss and optimizes heating efficiency of the heater 207, such that heat from the heater 207 gets transferred to the material (for example, the lost circulation material 110, the test fluid 111, or both) residing within the inner volume 101b and does not dissipate to the surrounding environment. The insulation jacket 209 can be made of, for example, fiberglass, mineral wool, cellulose, polyurethane foam, polystyrene, or natural fibers.

In an example experiment, two samples of the same lost circulation material 110 were tested. The first LCM was a dry sample that was tested at ambient temperature without exposure to a drilling fluid (such as the test fluid 111). The second LCM had the same composition as the first LCM, but was exposed to a drilling fluid (such as the test fluid 111) and heated to 200° F. during testing. The first and second LCMs were visually inspected and it was confirmed that the properties of the lost circulation material changes in the presence of drilling fluids and upon exposure to downhole conditions. For example, the elevated temperatures typical of downhole environments can soften or harden lost circulation materials. For example, the lost circulation material can chemically and/or physically interact with drilling fluid, which can alter the properties of the lost circulation material. Particle size analysis was performed on the first LCM before and after the pressure (stress) was applied. Particle size analysis was also performed on the second LCM before and after the exposure to downhole conditions (which also included pressurization/stress). The average diameter of the particles of the first LCM decreased from about 1000 micrometers to about 25 micrometers. The second LCM amalgamated into a solid slab after being exposed to downhole conditions (increased temperature and pressure, along with exposure to the test fluid 111). Further, upon visual inspection, the second LCM became darker in color in comparison to the first LCM that remained dry throughout the testing.

Figure 3A:
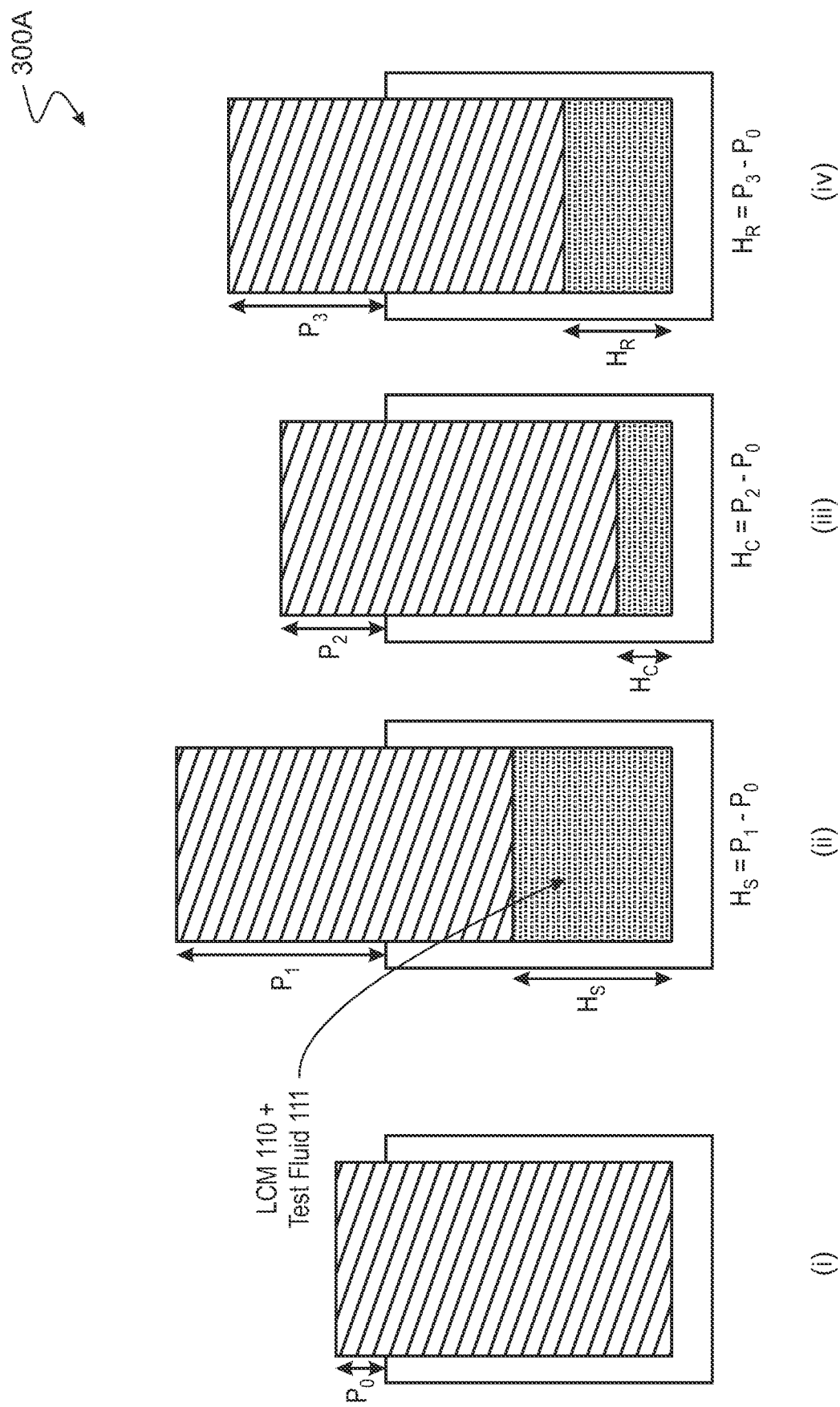
FIG. 3A is a progression of cross-sectional views of the apparatus of FIG. 1A during evaluation of a lost circulation material.

FIG. 3A is an example progression 300A of cross-sectional views of the apparatus 100 during evaluation of the lost circulation material 110. At (i), the piston 105 is in physical contact with the screen 103, and the inner volume 101b is substantially zero. An initial distance of the piston 105 extending from the top of the cylindrical wall 101 can be measured as $P_0$. At (ii), the apparatus 100 is loaded with the sample, which can include the lost circulation material 110 or both the lost circulation material 110 and the test fluid 111. The distance of the piston 105 extending from the top of the cylindrical wall 101 once the sample has been loaded into the apparatus 100 can be measured as $P_1$. The initial height ($H_S$) of the sample residing in the inner volume 101b can be calculated as the difference between $P_1$ and $P_0$ ($H_S=P_1-P_0$). At (iii), the motor 201 applies force on the piston 105 to pressurize the sample residing in the inner volume 101b to the specified test pressure mimicking downhole conditions. The distance of the piston 105 extending from the top of the cylindrical wall 101 once the sample has been pressurized to the specified test pressure can be measured as $P_2$. The height ($H_C$) of the compacted sample residing in the inner volume 101b can be calculated as the difference between $P_2$ and $P_0$ ($H_C=P_2-P_0$). At (iv), the motor 201 has released the force on the piston 105, and the sample residing in the inner volume 101b has been allowed to relax/expand. The distance of the piston 105 extending from the top of the cylindrical wall 101 once the sample has relaxed/expanded can be measured as $P_3$. The height ($H_R$) of the relaxed sample residing in the inner volume 101b can be calculated as the difference between $P_3$ and $P_0$ ($H_R=P_3-P_0$). The resiliency (% R) of the lost circulation material 110 can be calculated by Equation 1.

$$\% R = \left(\frac{H_R}{H_C} - 1\right) \times 100\% \quad (1)$$

Resiliency is defined as the extent to which a material (such as the lost circulation material 110) rebounds once an applied load has been removed.

Figure 3B:
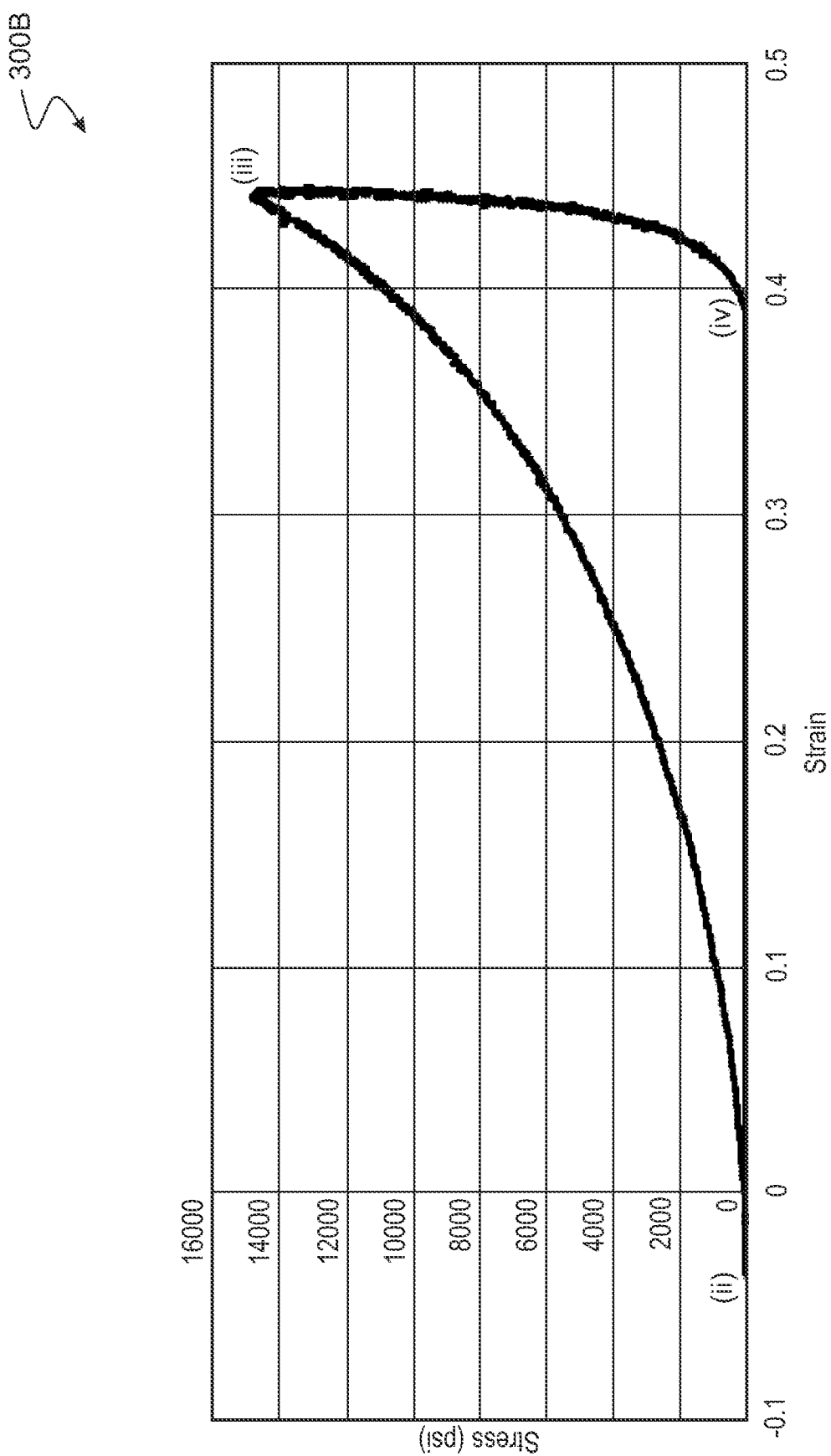
FIG. 3B is a plot of stress versus strain during evaluation of a lost circulation material.

FIG. 3B is an example plot 300B of stress versus strain during evaluation of an example lost circulation material. The plot 300B is labeled with (ii), (iii), and (iv) which correspond with the progression 300A shown in FIG. 3A. The initial height ($H_S$) of the sample residing in the inner volume 101b was calculated as 1.1455 inches (ii). The height ($H_C$) of the compacted sample residing in the inner volume 101b was calculated as 0.614372 inches (iii). The height ($H_R$) of the relaxed sample residing in the inner volume 101b was calculated as 0.673702 inches (iv). The resiliency (% R) of the example lost circulation material was calculated as 9.66%.

Figure 3C:
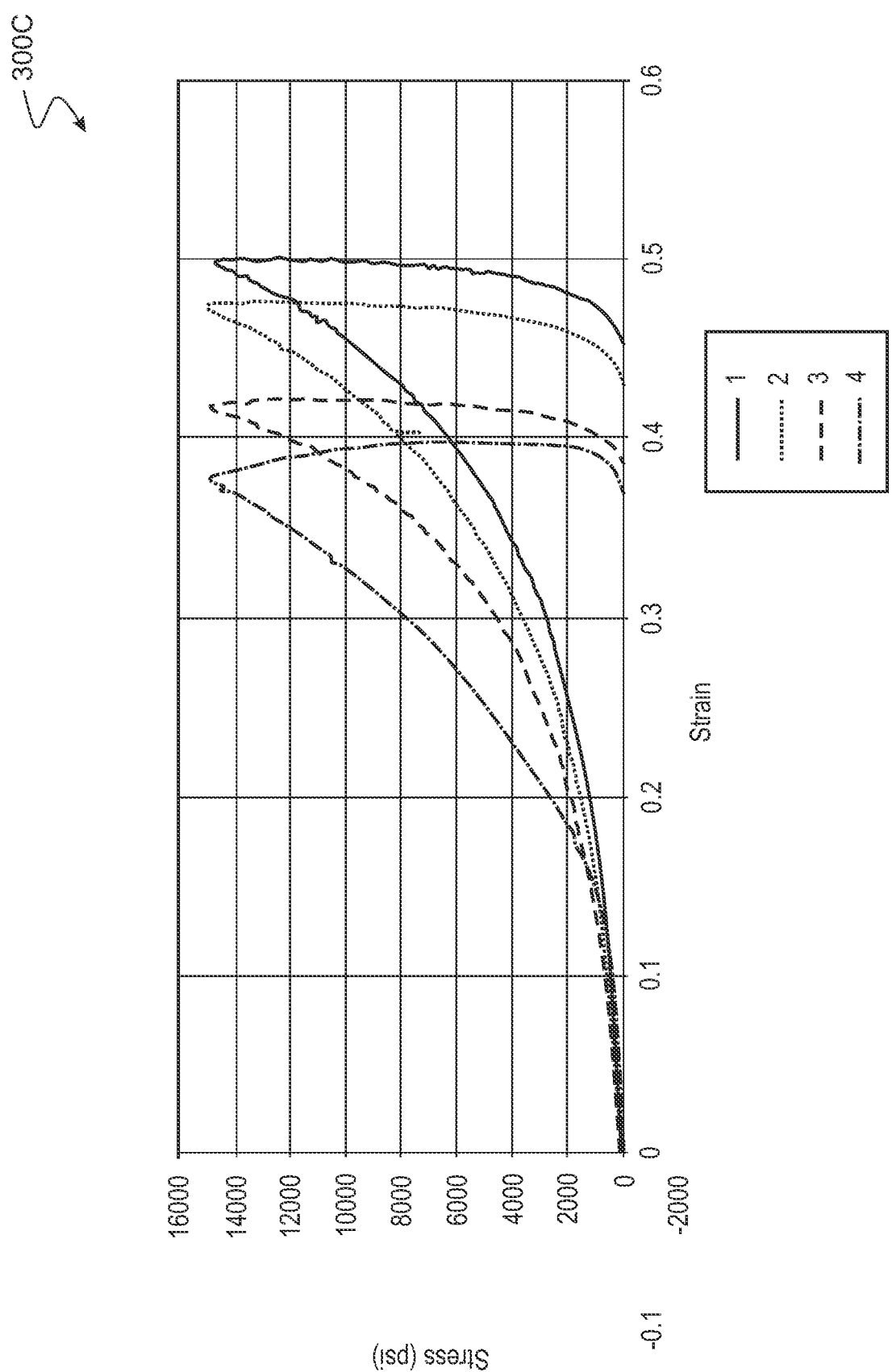
FIG. 3C is a plot of stress versus strain during evaluation of various lost circulation materials.

FIG. 3C is an example plot 300C of stress versus strain during evaluation of various example lost circulation materials. Curve 1 is the stress-strain curve for a first LCM that was dry and at ambient temperature. Curve 2 is the stress-strain curve for a second LCM that was dry and at elevated temperature (200° F.). Curve 3 is the stress-strain curve for a third LCM that was wetted with oil (for example, test fluid 111) and at ambient temperature. Curve 4 is the stress-strain curve for a fourth LCM that was wetted with oil (for example, test fluid 111) and at elevated temperature (200° F.). Table 1 shows data on the LCMs that were tested. It was observed that resiliency (% R) decreased with increased temperature. It was also observed that resiliency (% R) decreased in the presence of oil (test fluid 111). By considering the data in Table 1 with the plot 300C shown in FIG. 3C, it was observed that the shape of the stress-strain curve changes along with changes in resiliency. For example, with decreased resiliency (% R) (for example, due to increased temperature and/or exposure to oil), the stress-strain curve becomes more compressed with respect to the strain axis. Thus, the LCMs tested in this example became less resilient upon exposure to increased temperature and/or exposure to downhole fluids, such as oil (test fluid 111).

TABLE 1

LCM Test Data

| LCM Number | Specific Gravity | Weight (grams) | % R |
| --- | --- | --- | --- |
| 1 | 1.3 | 39 | 8.91 |
| 2 | 1.3 | 39 | 8.1 |
| 3 | 1.3 | 39 | 5.71 |
| 4 | 1.3 | 39 | 1.02 |

Figure 4:
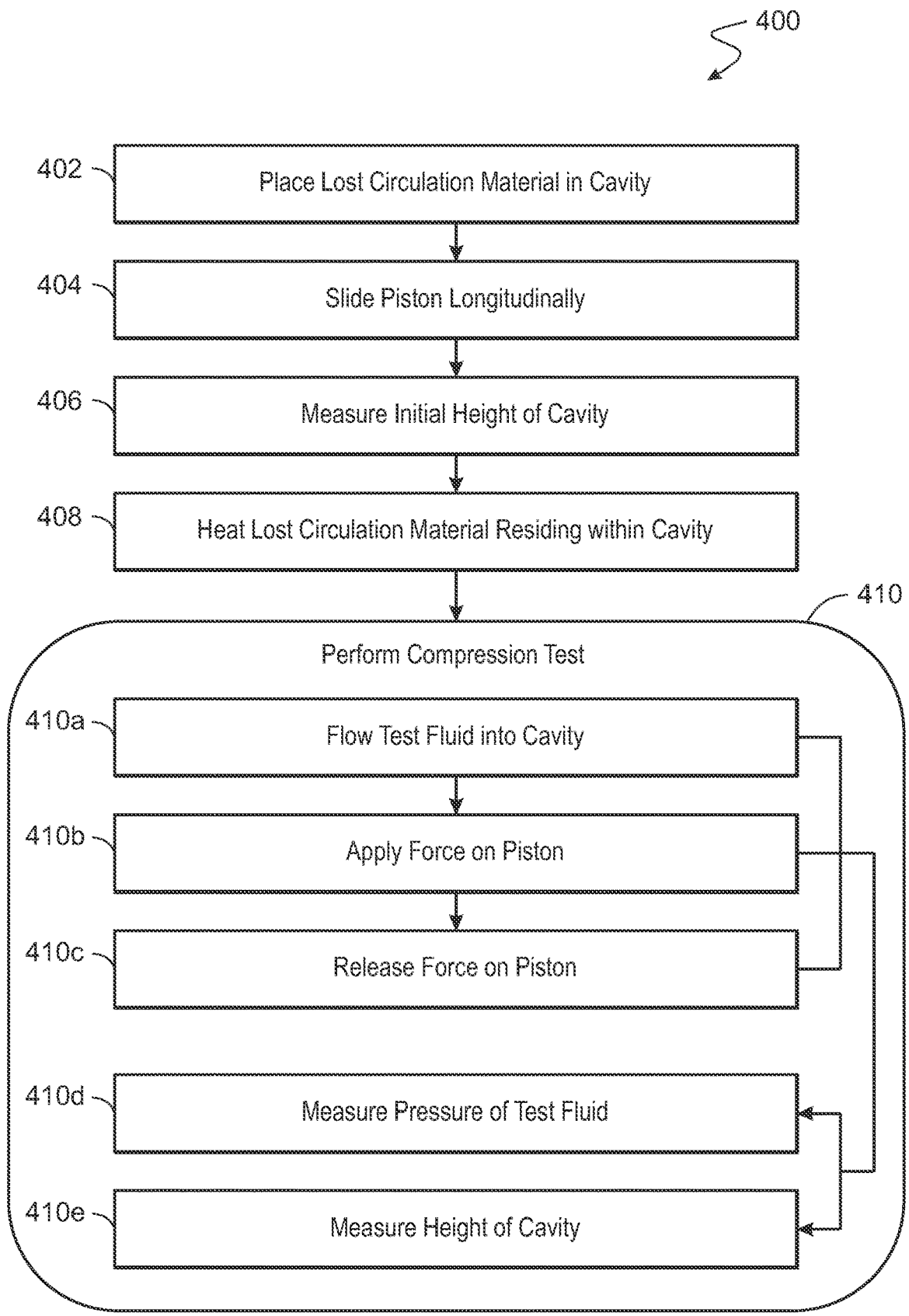
FIG. 4 is a flow chart of an example method for evaluating a lost circulation material.

FIG. 4 is a flow chart of an example method 400 for evaluating the lost circulation material 110. The system 200 can, for example, be used to implement the method 400. At block 402, a lost circulation material (such as the lost circulation material 110) is placed in a cavity of an apparatus (such as the inner volume 101b of the apparatus 100). As mentioned previously, the inner volume 101b is adjustable and defined by a portion of the inner bore 101a intermediate of the screen 103 and the piston 105. The height of the inner volume 101b is adjustable based on the piston 105 sliding longitudinally within the inner bore 101a away from or toward the screen 103. After placing the lost circulation material 110 in the inner volume 101b at block 402, the piston 105 is slid longitudinally at block 404, such that the piston 105 comes in contact with the lost circulation material 110 residing within the inner volume 101b. At block 406, an initial height of the inner volume 101b is measured (an example depicted by (ii) of progression 300A of FIG. 3A). At block 408, the lost circulation material 110 residing within the inner volume 101b is heated to a specified test temperature that mimics a downhole temperature. The lost circulation material 110 residing within the inner volume 101b can be heated to the specified test temperature at block 408, for example, by the heater 207. After the lost circulation material 110 residing within the inner volume 101b has reached the specified test temperature, a compression test 410 is performed on the lost circulation material 110 residing within the inner volume 101b.

The compression test 410 includes blocks 410a, 410b, 410c, 410d, and 410e. At block 410a, a test fluid (such as the test fluid 111) is flowed into the inner volume 101b, such that the test fluid 111 mixes with the lost circulation material 110 residing within the inner volume 101b. The test fluid 111 can be flowed into the inner volume 101b at block 410a, for example, by the pump 203 through the first port 102a. In some implementations, the first port 102a is closed (switched to the closed position) after the test fluid 111 is flowed into the inner volume 101b at block 410a and prior to proceeding to block 410b. At block 410b, force is applied on the piston 105 to pressurize the test fluid 111 residing within the inner volume 101b to a specified test pressure mimicking a downhole pressure. Force can be applied to the piston 105 at block 410b, for example, by the motor 201. The pump 203 at block 410a and the motor at block 410b can cooperate to pressurize the test fluid 111 to the specified test pressure. Closing the first port 102a prior to applying force on the piston 105 at block 410b can prevent the test fluid 111 from flowing out of the inner volume 101b through the first port 102a while the lost circulation material 110 and the test fluid 111 are being pressurized (compressed). After the test fluid 111 residing within the inner volume 101b has been pressurized to the specified test pressure, the force on the piston 105 is released at block 410c. Throughout the compression test 410, the pressure of the test fluid 111 residing within the inner volume 101b is measured at block 410d. Thus, the pressure of the test fluid 111 residing within the inner volume 101b is measured (410d) continuously throughout blocks 410a, 410b, and 410c. The pressure of the test fluid 111 residing within the inner volume 101b can be measured at block 410d, for example, by the pressure sensor 205 coupled to the second port 102b. Throughout the compression test 410, the height of the inner volume 101b is measured at block 410e. Thus, the height of the inner volume 101b is measured (410e) continuously throughout blocks 410a, 410b, and 410c. The height of the inner volume 101b can be measured at block 410e, for example, by measuring a distance of the piston 105 extending from the top of the cylindrical wall 101 and comparing that distance to an initial distance of the piston 105 extending from the top of the cylindrical wall 101 prior to the sample being loaded into the inner volume 101b at block 402. The heights/distances can be measured visually or by analyzing position data from the motor 201. For example, the motor 201 can transmit translation data representing how much the piston 105 has translated relative to a reference point. In some implementations, the pressure of the test fluid 111 residing within the inner volume 101b (410d) and the height of the inner volume 101b (410e) are continued to be measured until the test fluid 111 and the lost circulation material has completely relaxed and the height of the inner volume 101b has stopped changing after the force on the piston 105 has been released at block 410c. In some implementations, after the compression test has been performed at block 410, the first port 102a is opened and force is re-applied to the piston 105 to push the test fluid 111 out of the inner volume 101b through the first port 102a. The piston 105 can then be removed from the inner bore 101a, and the lost circulation material 110 can be removed from the apparatus 100. The lost circulation material 110 can be further evaluated if desired.

FIG. 5 is a block diagram of an example computer 500 used to provide computational functionalities associated with described algorithms, methods, functions, processes, flows, and procedures, as described in this specification, according to an implementation. The illustrated computer 500 is intended to encompass any computing device such as a server, desktop computer, laptop/notebook computer, one or more processors within these devices, or any other processing device, including physical or virtual instances (or both) of the computing device. Additionally, the computer 500 can include a computer that includes an input device, such as a keypad, keyboard, touch screen, or other device that can accept user information, and an output device that conveys information associated with the operation of the computer 500, including digital data, visual, audio information, or a combination of information.

The computer 500 includes an interface 504. Although illustrated as a single interface 504 in FIG. 5, two or more interfaces 504 may be used according to particular needs, desires, or particular implementations of the computer 500. Although not shown in FIG. 5, the computer 500 can be communicably coupled with a network. The interface 504 is used by the computer 500 for communicating with other systems that are connected to the network in a distributed environment. Generally, the interface 504 comprises logic encoded in software or hardware (or a combination of software and hardware) and is operable to communicate with the network. More specifically, the interface 504 may comprise software supporting one or more communication protocols associated with communications such that the network or interface's hardware is operable to communicate physical signals within and outside of the illustrated computer 500. The interface 504 can include a control interface, which can be used to couple the computer 500 to controls. In some implementations, the control interface is a bank of relays, a bank of MOSFET power controllers, a serial peripheral interface (SPI), or a Fieldbus, and the like. The interface 504 can include a sensor interface, which can be used to couple the computer 500 to sensors. In some implementations, the sensor interface is a bank of analog-to-digital converters (ADCs), and I2C bus, a serial peripheral interface (SPI) bus, or a Fieldbus, and the like. The interface 504 can include a human machine interface, which can be used by a user to interact with the computer 500. In some implementations, the human machine interface includes a monitor or a touch screen that is configured to display information, for example, to a user.

The computer 500 includes a processor 505. The processor 505 may be a microprocessor, a multi-core processor, a multithreaded processor, an ultra-low-voltage processor, an embedded processor, or a virtual processor. In some embodiments, the processor 505 may be part of a system-on-a-chip (SoC) in which the processor 505 and the other components of the computer 500 are formed into a single integrated electronics package. In some implementations, the processor 505 may include processors from Intel® Corporation of Santa Clara, California, from Advanced Micro Devices, Inc. (AMD) of Sunnyvale, California, or from ARM Holdings, LTD., Of Cambridge, England. Any number of other processors from other suppliers may also be used. Although illustrated as a single processor 505 in FIG. 5, two or more processors may be used according to particular needs, desires, or particular implementations of the computer 500. Generally, the processor 505 executes instructions and manipulates data to perform the operations of the computer 500 and any algorithms, methods, functions, processes, flows, and procedures as described in this specification. The processor 505 may communicate with other components of the computer 500 over a bus. The bus may include any number of technologies, such as industry standard architecture (ISA), extended ISA (EISA), peripheral component interconnect (PCI), peripheral component interconnect extended (PCIx), PCI express (PCIe), or any number of other technologies. The bus may be a proprietary bus, for example, used in an SoC based system. Other bus technologies may be used, in addition to, or instead of, the technologies above.

The computer 500 can also include a database 506 that can hold data for the computer 500 or other components (or a combination of both) that can be connected to the network. Although illustrated as a single database 506 in FIG. 5, two or more databases (of the same or combination of types) can be used according to particular needs, desires, or particular implementations of the computer 500 and the described functionality. While database 506 is illustrated as an integral component of the computer 500, database 506 can be external to the computer 500. The database 506 can be used for the persistent storage of information, such as data, applications, operating systems, and so forth. The database 506 may be a nonvolatile RAM, a solid-state disk drive, or a flash drive, among others. In some implementations, the database 306 will include a hard disk drive, such as a micro hard disk drive, a regular hard disk drive, or an array of hard disk drives, for example, associated with a DCS or a cloud server.

The computer 500 also includes a memory 507 that can hold data for the computer 500 or other components (or a combination of both) that can be connected to the network. Although illustrated as a single memory 507 in FIG. 5, two or more memories 507 (of the same or combination of types) can be used according to particular needs, desires, or particular implementations of the computer 500 and the described functionality. While memory 507 is illustrated as an integral component of the computer 500, memory 507 can be external to the computer 500. The memory 507 can be a transitory or non-transitory storage medium. In some implementations, such as in PLCs and other process control units, the memory 507 is integrated with the database 506 used for long-term storage of programs and data. The memory 507 can include any number of volatile and non-volatile memory devices, such as volatile random-access memory (RAM), static random-access memory (SRAM), flash memory, and the like. In smaller devices, such as PLCs, the memory 507 may include registers associated with the processor 505 itself.

The memory 507 stores computer-readable instructions executable by the processor 505 that, when executed, cause the processor 505 to perform operations, such as transmitting a temperature adjustment signal to the heater 207 to cause the heater 207 to heat the lost circulation material 110 residing within the inner volume 101b to a specified test temperature that mimics a downhole temperature and performing a compression test on the lost circulation material 110 residing within the inner volume 101b. The compression test can include transmitting a pumping signal to the pump 203 to cause the pump 203 to flow the test fluid 111 into the inner volume 101b, such that the test fluid 111 mixes with the lost circulation material 110 residing within the inner volume 101b. The compression test can include transmitting a start signal to the motor 201 to cause the motor 201 to apply force on the piston 105 to slide the piston 105 longitudinally within the inner bore 101b toward the screen 103, thereby pressurizing the lost circulation material 110 and the test fluid 111 residing within the inner volume 101b to a specified test pressure that mimics a downhole pressure. The compression test can include, after the lost circulation material 110 and the test fluid 111 residing within the inner volume 101b have been pressurized to the specified test pressure, transmitting a stop signal to the motor 201 to cause the motor 201 to release the force on the piston 105, thereby allowing the lost circulation material 110 and the test fluid 111 residing within the inner volume 101b to de-pressurize (relax/expand). The operations can include, throughout the compression test, receiving a position signal from the motor 201. The position signal can represent a longitudinal position of the piston 105 within the inner bore 101b relative to the screen 103. The operations can include, throughout the compression test, determining and recording (to the memory 507) a height of the inner volume 101b based on the received position signal from the motor 201. The operations can include, throughout the compression test, receiving a pressure signal from the pressure sensor 205. The pressure signal can represent an operating pressure of the lost circulation material 110 and the test fluid 111 residing within the inner volume 101b. The operations can include, throughout the compression test, recording (to the memory 507) the operating pressure of the lost circulation material 110 and the test fluid 111 residing within the inner volume 101b. The operations can include generating a plot of the recorded pressures (stress) versus the recorded heights of the inner volume (strain) for the compression test. The operations can include displaying the generated plot on a screen (for example, the interface 504) that is communicatively coupled to the processor 505.

The computer 500 can also include a power supply 514. The power supply 514 can include a rechargeable or non-rechargeable battery that can be configured to be either user- or non-user-replaceable. The power supply 514 can be hard-wired. There may be any number of computers 500 associated with, or external to, a computer system containing computer 500, each computer 500 communicating over the network. Further, the term "client," "user," "operator," and other appropriate terminology may be used interchangeably, as appropriate, without departing from this specification. Moreover, this specification contemplates that many users may use one computer 500, or that one user may use multiple computers 500.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features may be described as acting in certain combinations and even initially claimed as such, one or more features from a claimed combination can, in some cases, be excised from the combination, and the claimed combination may be directed to a sub-combination or variation of a subcombination.

As used in this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described components and systems can generally be integrated together or packaged into multiple products.

Accordingly, the previously described example implementations do not define or constrain the present disclosure. Other changes, substitutions, and alterations are also possible without departing from the spirit and scope of the present disclosure.

What is claimed is:

1. A method comprising:
    placing a lost circulation material in a cavity of an apparatus, wherein a volume of the cavity is adjustable, the cavity defined by an inner bore of a cylindrical wall of the apparatus, intermediate of a piston of the apparatus and a screen of the apparatus, wherein a distance between the piston and the screen is defined as the height of the cavity, and the height of the cavity is adjustable based on the piston sliding longitudinally within the inner bore away from or toward the screen;
    after placing the lost circulation material in the cavity, sliding the piston longitudinally, such that the piston comes in contact with the lost circulation material residing within the cavity;
    measuring an initial height of the cavity;
    heating the lost circulation material residing within the cavity to a specified test temperature mimicking a downhole temperature; and
    after the lost circulation material residing within the cavity has reached the specified test temperature, performing a compression test on the lost circulation material residing within the cavity, the compression test comprising:
        flowing a test fluid into the cavity, such that the test fluid mixes with the lost circulation material residing within the cavity;
        applying force on the piston to pressurize the test fluid residing within the cavity to a specified test pressure mimicking a downhole pressure;
        after the test fluid residing within the cavity has been pressurized to the specified test pressure, releasing the force on the piston;
        throughout the compression test, measuring pressure of the test fluid residing within the cavity; and
        throughout the compression test, measuring the height of the cavity.

2. The method of claim 1, comprising generating a plot of the measured pressures of the test fluid residing within the cavity as stress versus the measured heights of the cavity as strain for the compression test.

3. The method of claim 2, wherein the apparatus comprises a first port extending through the cylindrical wall, and the test fluid is flowed into the cavity through the first port by a pump.

4. The method of claim 3, wherein the force is applied on a first end of the piston by a linear actuator, and the pump flowing the test fluid and the linear actuator applying force on the piston cooperate to pressurize the test fluid residing within the cavity to the specified test pressure mimicking the downhole pressure.

5. The method of claim 4, comprising closing the first port after flowing the test fluid into the cavity and prior to applying force on the piston, thereby preventing the test fluid from flowing out of the cavity through the first port.

6. The method of claim 5, wherein:
    the apparatus comprises a base coupled to the cylindrical wall;
    at least a portion of the base is disposed within the inner bore;
    the screen is coupled to the base and spans a cross-sectional area of the inner bore;
    the apparatus comprises a second port that extends through the base and passes through the screen; and
    the pressure of the test fluid residing within the cavity is measured by a pressure sensor coupled to the second port.

7. The method of claim 6, wherein the apparatus comprises:
    a first sealing element wrapping around the piston, wherein the first sealing element forms a first seal between the piston and the cylindrical wall to prevent leakage of the test fluid from the cavity through the first seal, and the first seal remains intact while the piston slides longitudinally within the inner bore; and
    a second sealing element wrapping around the portion of the base that is disposed within the inner bore, wherein the second sealing element forms a second seal between the base and the cylindrical wall to prevent leakage of the test fluid from the cavity through the second seal.

8. The method of claim 7, comprising, after performing the compression test on the lost circulation material residing within the cavity, opening the first port and applying force on the piston to push the test fluid out of the cavity through the first port.

9. The method of claim 8, wherein the test fluid is a drilling mud.

10. The method of claim 9, wherein the first port is sized to prevent the lost circulation material from exiting the cavity through the first port.

11. The method of claim 10, wherein the lost circulation material is heated to the specified test temperature mimicking the downhole temperature by a heater wrapped around an outer circumferential surface of the cylindrical wall, and the method comprises mitigating, by an insulating jacket surrounding the heater, heat from the heater dissipating to a surrounding environment.

12. A system comprising:
an apparatus comprising:
  a cylindrical wall defining an inner bore;
  a screen disposed within the inner bore; and
  a piston sized to fit within the inner bore, wherein a portion of the inner bore that is intermediate of the screen and the piston is defined as an inner volume of the apparatus for holding a lost circulation material and a test fluid, the inner volume being variable based on a longitudinal position of the piston within the inner bore relative to the screen;
a motor coupled to the piston;
a pump coupled to the cylindrical wall;
a pressure sensor coupled to the apparatus;
a heater coupled to the cylindrical wall; and
a computer comprising:
  a processor communicatively coupled to the motor, the pump, the heater, and the pressure sensor; and
  a computer-readable storage medium coupled to the processor and storing programming instructions for execution by the processor, the programming instructions instructing the processor to perform operations comprising:
    transmitting a temperature adjustment signal to the heater to cause the heater to heat the lost circulation material residing within the inner volume to a specified test temperature mimicking a downhole temperature;
    performing a compression test on the lost circulation material residing within the inner volume, the compression test comprising:
      transmitting a pumping signal to the pump to cause the pump to flow the test fluid into the inner volume, such that the test fluid mixes with the lost circulation material residing within the inner volume;
      transmitting a start signal to the motor to cause the motor to apply force on the piston to slide the piston longitudinally within the inner bore toward the screen, thereby pressurizing the test fluid and the lost circulation material residing within the inner volume to a specified test pressure mimicking a downhole pressure;
      after the test fluid and the lost circulation material residing within the inner volume have been pressurized to the specified test pressure, transmitting a stop signal to the motor to cause the motor to release the force on the piston, thereby allowing the test fluid and the lost circulation material residing within the inner volume to de-pressurize;
    throughout the compression test:
      receiving a position signal from the motor, the position signal representing a longitudinal position of the piston within the inner bore relative to the screen;
      determining and recording, to the storage medium, a height of the inner volume based on the received position signal from the motor;
      receiving a pressure signal from the pressure sensor, the pressure signal representing an operating pressure of the test fluid and the lost circulation material residing within the inner volume; and
      recording, to the storage medium, the operating pressure of the test fluid and the lost circulation material residing within the inner volume.

13. The system of claim 12, wherein the operations comprise generating a plot of the recorded pressures as stress versus the recorded heights of the inner volume as strain for the compression test and displaying the plot on a screen communicatively coupled to the processor.

14. The system of claim 13, wherein the apparatus comprises:
a base coupled to the cylindrical wall, wherein at least a portion of the base is disposed within the inner bore;
a first O-ring wrapping around an outer circumferential wall of the piston; and
a second O-ring wrapping around the portion of the base that is disposed within the inner bore.

15. The system of claim 14, wherein the heater wraps around an outer circumferential surface of the cylindrical wall, and the system comprises an insulating jacket surrounding the heater, the insulating jacket configured to mitigate heat from the heater dissipating to a surrounding environment.

16. The system of claim 15, wherein the base is coupled to the cylindrical wall by a threaded bolt.

17. The system of claim 16, comprising:
a reservoir configured to hold a specified amount of the test fluid; and
a piping network comprising:
  a suction piping fluidically connecting the reservoir to the pump; and
  a discharge piping fluidically connecting the pump to the cylindrical wall.

18. The system of claim 17, wherein the piping network comprises a bypass piping fluidically connecting the reservoir to the cylindrical wall, the bypass piping configured to flow test fluid from the inner volume back to the reservoir.

19. The system of claim 18, wherein the test fluid is a drilling mud.

* * * * *